United States Patent
Zheng et al.

(10) Patent No.: US 9,924,945 B2
(45) Date of Patent: Mar. 27, 2018

(54) SURGICAL APPARATUS ACTUATOR

(71) Applicant: SHANGHAI YISI MEDICAL TECHNOLOGY CO., LTD, Shanghai (CN)

(72) Inventors: Minhua Zheng, Shanghai (CN); Xinliang Zhang, Shanghai (CN); Anhua Li, Shanghai (CN); Bo Feng, Shanghai (CN); Junjun Ma, Shanghai (CN); Jing Sun, Shanghai (CN)

(73) Assignee: SHANGHAI YISI MEDICAL TECHNOLOGY CO., LTD, Shanghai (CN)

( * ) Notice: Subject to any disclaimer, the term of this patent is extended or adjusted under 35 U.S.C. 154(b) by 444 days.

(21) Appl. No.: 14/429,358

(22) PCT Filed: Aug. 22, 2013

(86) PCT No.: PCT/CN2013/082025
§ 371 (c)(1),
(2) Date: Mar. 18, 2015

(87) PCT Pub. No.: WO2014/044108
PCT Pub. Date: Mar. 27, 2014

(65) Prior Publication Data
US 2015/0230795 A1 Aug. 20, 2015

(30) Foreign Application Priority Data
Sep. 18, 2012 (CN) .......................... 2012 1 0349356

(51) Int. Cl.
*A61B 17/072* (2006.01)

(52) U.S. Cl.
CPC .............. *A61B 17/07207* (2013.01); *A61B 2017/07214* (2013.01)

(58) Field of Classification Search
CPC .................. A61B 17/07207; A61B 17/115
USPC ........................................ 227/176.1
See application file for complete search history.

(56) References Cited

U.S. PATENT DOCUMENTS

| 5,173,133 A * | 12/1992 | Morin .................. A61B 17/072 148/567 |
| 5,308,576 A * | 5/1994 | Green .............. A61B 17/07207 227/175.1 |
| 5,865,361 A * | 2/1999 | Milliman ......... A61B 17/07207 227/176.1 |
| 2005/0145671 A1* | 7/2005 | Viola ............... A61B 17/00491 227/175.1 |

(Continued)

*Primary Examiner* — Nathaniel Chukwurah (57) ABSTRACT

An improved surgical apparatus actuator includes a nail bin assembly (1002), a nail anvil assembly (1001) connecting with the nail bin assembly (1002), and a drive assembly (1003) controlling the nail bin assembly (1002) and the nail anvil assembly (1001) to convert between opening and closing conditions. The nail anvil assembly (1001) includes a nail anvil plate (103) and a nail anvil seat (102), wherein the nail anvil plate (103) is provided on an inner side (1022) of the nail anvil seat (102), the nail anvil seat (102) has the structure, material and processing technology capable of providing high anti-bending performance, the nail anvil plate (103) is cold-punched from a thinner stainless steel sheet. Therefore, the processing difficulty of the components is reduced, and meanwhile, the ability of the actuator chuck to resist bending deformation is improved.

11 Claims, 6 Drawing Sheets

(56) References Cited

U.S. PATENT DOCUMENTS

2008/0078801 A1* 4/2008 Shelton ............... A61B 17/072
                                                    227/175.1
2009/0206131 A1* 8/2009 Weisenburgh, II
                              ..................... A61B 17/07207
                                                    227/175.2

* cited by examiner

SURGICAL APPARATUS ACTUATOR

CROSS REFERENCE OF RELATED APPLICATION

This is a U.S. National Stage under 35 U.S.C 371 of the International Application PCT/CN2013/082025, filed Aug. 22, 2013, which claims priority under 35 U.S.C. 119(a-d) to CN 201210349356.7, filed Sep. 18, 2012.

BACKGROUND OF THE PRESENT INVENTION

Field of Invention

This invention relates to a surgical apparatus, especially a kind of anastomat for surgical operation. More specifically, it relates to an improved surgical apparatus actuator.

Description of Related Arts

The working principle of surgical anastomat is to clamp tissues through the closing of two corresponding jaws (which are normally called nail anvil assembly and nail bin assembly) and then push the metal suturing nails in the anastomat nail bin out for molding and suture tissues together. In some anastomats, a cutter is installed to cut off sutured tissues.

The anastomat with the above functions also includes actuator, intermediate connecting body and controller. The actuator consists of nail anvil assembly, nail bin assembly and drive assembly. The nail anvil assembly includes a nail molding surface which contains multiple rows of nail grooves. The nail groove is used for metal suturing nail molding. The nail bin assembly usually consists of nail bin, suturing nail, nail push block and nail push slide and nail bin seat. The upper surface of the nail bin is the tissue contact surface and the nail bin is installed in the nail bin seat. The nail anvil assembly connects at the near end with the near end of the nail bin assembly in a mobile manner and converts between the opening condition and closing condition. The drive assembly connects with the drive mechanism and is used to convert the triggering operation into actuator closing, triggering and opening operations. Generally, each of the nail anvil assembly and nail bin seat contains also a longitudinal groove. The above longitudinal groove is used to accommodate the drive assembly to allow it to pass. When the drive assembly moves toward the far end of the actuator through the above longitudinal groove, it drives the nail anvil assembly and nail bin assembly to convert from the opening condition to closing condition and drives the nail push slide and nail push block to push out suturing nails for molding in the nail groove of the nail molding surface of the nail anvil assembly. Generally, the drive assembly also includes a cutter, which is used to cut tissues among multiple rows of nail threads after tissues are sutured by suturing nails. The controller is used to control the apparatus operation manually, which usually consists of a fixed handle, a trigger connecting with the fixed handle in a relatively mobile manner and a group of drive mechanisms transmitting the triggering operation to the actuator. The intermediate connecting body connects with the far end of controller in a mobile manner and connects with the near end of the actuator. The intermediate connecting body constitutes a connecting passageway to transmit the triggering operation to the actuator.

The Endo GIA Universal cutting anastomat from Tyco Healthcare in USA (renamed as Covidien later) and the Echelon cutting anastomat from Ethicon Endo-Surgery in USA are the representative products achieving the above functions. The above products have been sold for years and proved by market as having a good clinical application effect. The actuators of the blue nail bins of the above products can compress human body tissues (such as stomach tissues, lung tissues, intestine tissues, etc.) from a natural thickness of 5 mm-8 mm to a closing thickness of 1.5 mm when the nail anvil assembly and nail bin assembly close. In terms of the product function, the tissue closing thickness should be uniform from the near end of the nail anvil to the far end thereof so as to ensure suturing nails to be highly uniform in molding. Suturing effect can be guaranteed only when suturing nails suture tissues with a stable quality. Therefore, the nail anvil assembly needs to have a high bending strength. In nail anvil assembly manufacturing, the nail groove has a substantial material displacement in mould punching molding and this objectively requires that the material of the nail anvil assembly has good flowability and is easy to create a large-scale plastic deformation. The requirements of the nail anvil assembly for material plasticity and bending strength are contradictory. The technical proposals adopted by the Endo GIA Universal cutting anastomat and the Echelon cutting anastomat solve the above contradiction satisfactorily. However, there are still places requiring perfection, for example: the bending strength of the nail anvil assembly of the Endo GIA Universal cutting anastomat is still not high enough in some clinical applications and the processing technology is highly difficult; the bending strength of the Echelon cutting anastomat is enough, however, the processing technology is complicated with a high cost.

For example, in U.S. Pat. No. 5,865,361, Tyco Healthcare described the nail anvil assembly of the Endo GIA Universal cutting anastomat. By referring to the description in U.S. Pat. No. 5,865,361 and combining with the design adopted for the real product being sold on market, the nail anvil assembly is welded from nail anvil plate and back cover plate. The empty cavity formed between the upper surface of the back cover plate and the nail anvil plate is the space for cutter holder pin to slide. The function of the back cover plate is to prevent tissues from being injured as a result of pinching by the cutter holder pin in the process of the nail anvil assembly closing tissues and anastomosing. The back cover plate is punched from 0.2 mm-0.3 mm thick stainless steel sheet. The nail anvil plate is punched from stainless steel sheet around 1 mm thick. Both the two spare parts use 304 stainless steel which can be strengthened through heat treatment and can exhibit a conspicuous machining hardening in the process of machining. On the lower surface of the nail anvil plate, a lot of nail grooves formed from cold punching process are distributed. For the Endo GIA Universal nail anvil plate with a 45 mm nail thread specification, 6 rows×11=66 nail grooves with a depth around 0.5 mm are punched (coldly) on the 45 mm×9 mm plane. The nail groove depth reaches half of the nail anvil plate material thickness. This results in the surface of material that the nail anvil plate and the mould punch top contact having serious machining hardening in nail groove cold punch molding, which prevents nail grooves from further molding and also results in aggravated wearing to the mould punch and mould life reduction and thus results in greater nail groove dimension fluctuation, accuracy reduction and eventual influence on the suturing nail molding quality.

With regard to the above difficulties in nail groove molding, it is speculated that in manufacturing the nail anvil plate of the Endo GIA Universal cutting anastomat, the nail anvil plate uses 304 stainless steel sheet in annealed state to reduce maximally the initial material hardness, upgrade the nail groove molding accuracy and mould life. However, the bending strength of the nail anvil plate made of 304 stainless steel in annealed state is reduced and that thus results in the bending strength of the nail anvil assembly being low. As a result, when that product is applied to some thick tissue anastomosing and cutting occasions, the nail anvil assembly has a serious bending deformation after the nail anvil assembly and nail bin assembly close. As a result, it is unable to ensure the tissues clamped in the jaw to be consistent in compression thickness. Especially, the tissues at the far end of the jaw have an unsatisfactory closing effect due to incomplete compression. This results in tissues being easy to overflow toward the far end of the jaw in cutting and the tissue width after anastomosing being greater than the original tissue compression length. In some cases, it may result in having to increase the amount of nail bins, which implies the increase in medical cost; when serious, it may result in poor suturing nail molding.

SUMMARY OF THE PRESENT INVENTION

With regard to the defects in the existing technology, the purpose of this invention is to provide an improved surgical apparatus actuator and an anastomat containing the actuator. According to the apparatus (i.e. anastomat) provided by this invention, tissue clamping can be achieved and the molding of at least one row of suturing nails can be achieved; in some application conditions, tissue cutting can also be achieved. Tissues can be cut open between multiple rows of suturing nail threads.

According to one aspect of this invention, an improved surgical apparatus actuator is provided, including a nail bin assembly, a nail anvil assembly connecting with the nail bin assembly, and a drive assembly controlling the nail bin assembly and nail anvil assembly to convert opening and closing conditions. The nail anvil assembly includes a nail anvil plate and a nail anvil seat. The nail anvil plate is provided on an inner side face of the nail anvil seat. The nail anvil plate is cold-punched from stainless steel sheet. A thickness of the stainless steel sheet is lower than a maximum molding depth of nail grooves of the nail anvil plate. The nail anvil plate has a first guide groove provided thereon. The nail anvil seat has a second guide groove provided thereon. The first guide groove and the second guide groove are arranged coaxially. The drive assembly slides under a guide of the first guide groove and the second guide groove.

Preferably, the nail anvil plate is punched and drawn from stainless steel sheet.

Preferably, the thickness of the stainless steel sheet is 0.1-0.4 mm.

Preferably, the thickness of the stainless steel sheet is 0.2-0.3 mm.

Preferably, a tensile strength of a material used by the nail anvil seat is higher than that of the stainless steel sheet.

Preferably, the nail anvil seat is processed by a method selected from a group consisting of thermal forging, powder metallurgical molding, casting and mechanical cutting. In which, the powder metallurgical molding process includes metal injection molding technology (MIM) and metal compression molding technology.

Preferably, a back cover plate is also included, in which, the back cover plate is provided on an outer side face of the nail anvil seat. The outer side face of the nail anvil seat has a guide rail surface. An empty cavity exists between the back cover plate and the guide rail surface of the nail anvil seat. The drive assembly moves along the guide rail surface in the empty cavity.

Preferably, all components of the nail anvil assembly are connected to form an integral structure through welding and/or mechanical riveting.

Preferably, the nail grooves on the nail anvil plate are arranged in multiple rows of parallel straight lines or parallel curves selectively.

Preferably, the nail grooves on the nail anvil plate are arranged into 4 rows or 6 rows.

According to another aspect of this invention, an improved surgical apparatus is also provided, including a controller, an intermediate connecting body and an actuator, in which the actuator, the intermediate connecting body and the controller are connected in sequence.

In comparison with the existing technology, this invention has the following beneficial effects:

1. It mainly uses the nail anvil plate and nail anvil seat made of different materials to constitute the nail anvil assembly. As a result, the requirements of the nail anvil assembly for both material plasticity and bending strength are met. In which, the nail anvil plate uses thin stainless steel sheet for molding through tensile process to improve the difficulty in nail groove molding and provide nail grooves with a high accuracy; the nail anvil seat adopts a structural, material and processing proposal being able to provide a high bending strength to provide a strong bending property to the whole nail anvil assembly;

2. The tensile strength of the material used by the nail anvil seat is higher than that of the material used by the nail anvil plate, which enables the nail anvil seat to provide a higher tensile strength and a higher bending strength that makes the nail anvil plate easier for molding through drawing. As a result, the problem of tissue overflow and poor suturing nail molding due to insufficient bending strength of the nail anvil assembly existing in the exist apparatus is overcome.

3. The nail anvil assembly is combined by multiple components with different functions, which enhances the uniformity of the clamped tissues in thickness when the actuator closes tissues. In comparison with the existing product design proposals, the closing effect of the actuator is better, the manufacturing cost is lower and the clinical risk is smaller.

4. When the thickness t of the stainless steel sheet for processing the nail anvil plate is less than the maximum molding depth h of nail groove, the cold punching process for processing the nail anvil plate can use punch drawing process in place of the impressing process used in nail groove molding on thick sheet. As a result, the nail groove dimension accuracy is increased.

BRIEF DESCRIPTION OF THE DRAWINGS

By reading and referring to the detailed descriptions made by following figures to the unlimited embodiment, other characteristics, purposes and advantages of this invention will become more conspicuous.

DETAILED DESCRIPTION OF THE PREFERRED EMBODIMENT

A detailed description to this invention is to be made in combination with embodiments below. The following embodiment will help the technical people in this field to further understand this invention. However, it does not limit this invention in any form. What should be pointed out is that the ordinary technical people in this field can make a number of variations and improvements under the prerequisite not being divorced from the conception of this invention. All these belong to the protection scope of this invention.

This invention applies to the actuator of surgical apparatus, uses a special spare part combination proposal, material combination proposal and processing technique proposal to manufacture the actuator to obtain a nail anvil assembly with a better comprehensive bending strength.

FIG. 1 to FIG. 10 show the schematic diagrams for the surgical apparatus improved according to the first embodiment of this invention. Specifically, in this embodiment, referring to FIG. 1-FIG. 2, the improved surgical apparatus includes a controller 300, an intermediate connecting body 200 and an actuator 100, in which the actuator 100, the intermediate connecting body and the controller 300 are connected in sequence.

Figure 2:
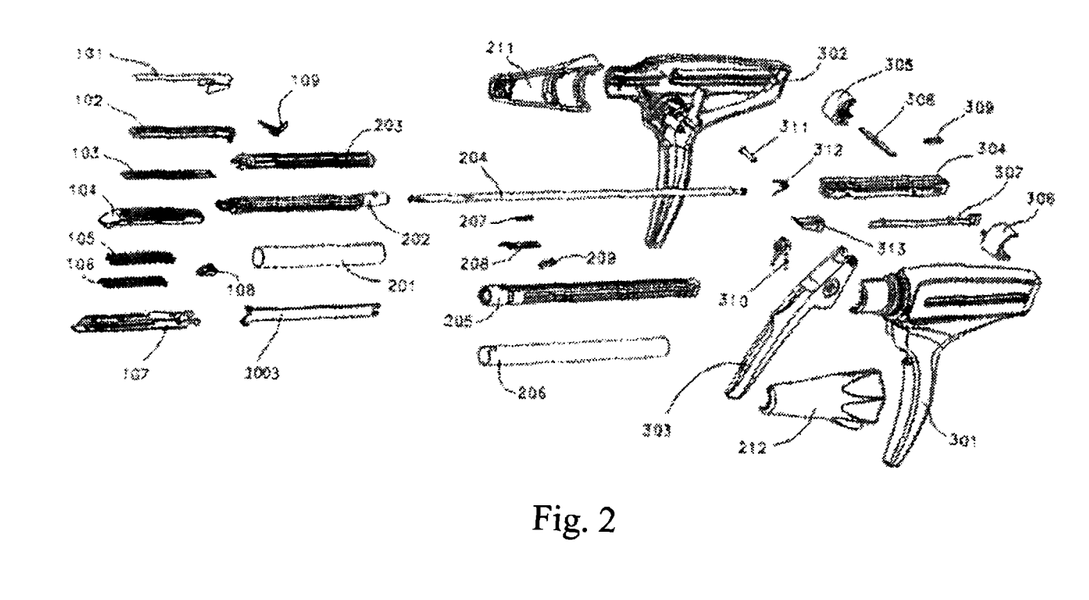
FIG. 2 is an exploded structural schematic diagram for the surgical apparatus as shown in FIG. 1.

The controller 300 usually includes a first fixed handle 301, a second fixed handle 302, a mobile trigger 303, a trigger reset spring 310 and a drive and motion transfer mechanism transmitting a rotary motion of the trigger 303 to a drive rod 204 of the intermediate connecting body 200 and driving the drive rod 204 to make a straight line motion longitudinally. As shown in FIG. 2, the drive and motion transfer mechanism includes a pullout gear 313, a pullout gear pin 311, a pullout gear spring 312 and a rack 304. The rack 304 can be installed in a reciprocating manner in a guide rail inside the first fixed handle 301 and the second fixed handle 302. The pullout gear 313 can be installed in a rotary motion manner at one end of the trigger 303 through the pullout gear pin 311. The pullout gear spring 312 keeps the pullout gear 313 deviating all the time for engagement with the rack 304. When operating the trigger 303, the rotary motion of the trigger 303 is transmitted to the rack 304 through the pullout gear 313 to drive the rack 304 to make a straight line motion toward a far end. Usually, the controller 300 also includes a set of rack reset mechanism to reset the rack 304 after completing an apparatus function. As shown in FIG. 2, the rack reset mechanism includes a first reset cap 305, a second reset cap 306, a reset pin 308, a rack reset spring 309 and a pullout gear disengagement plate 307. When the rack 304 is divorced from an initial position due to operating the trigger 303, an operator pulls the first reset cap 305, the second reset cap 306 toward a near end and drive the first pullout gear disengagement plate 307 to move through the reset pin 308 and bring along the pullout gear 313 to be divorced from a position engaging with the rack 304; when continuing to pull the first reset cap 305 and the second reset cap 306, the reset pin 308 continues to draw back until the reset pin 308 and the rack 304 contact rigidly. When continuing to pull the first reset cap 305, the second reset cap 306 toward the near end at this point, the rack 304 will move toward the near end with the reset pin 308 until reset.

The intermediate connecting body 200 is connected at a far end of the controller 300. In the surgical anastomat embodiment as shown in FIG. 2, the intermediate connecting body 200 includes: a first rotating joint 211, a second rotating joint 212, a drive rod 204, a gun pipe 205, a gun casing pipe 206, a first nail box inner pipe 202, a second nail box inner pipe 203, a nail box casing pipe 201, etc. An axis of the gun pipe 205, the first nail box inner pipe 202 and the second nail box inner pipe 203 are co-axial and a direction of the axis constitutes the longitudinal direction of this embodiment. A near end of the gun pipe 205 is connected with the far end of the controller 300 through the first rotating joint 211, the second rotating joint 212 in a mobile manner. The drive rod 204 is arranged in inner cavities of the gun pipe 205 and the first nail box inner pipe 202, the second nail box inner pipe 203, and can make a free motion longitudinally in the inner cavities of the gun pipe 205 and the first nail box inner pipe 202, the second nail box inner pipe 203. The far end of the drive rod 204 connects with a near end of the drive assembly 109. The near end of the drive rod 204 connects with the rack 304. The drive rod 204 can transmit the longitudinal motion of the rack 304 to the drive assembly 109.

In the surgical anastomat embodiments as shown in FIG. 2, the intermediate connecting body 200 also includes a loading safety mechanism which can unload with the actuator 100, including: a load reset spring 207, a load safety block 208 and a load limit block 209. After the actuator 100 and the intermediate connecting body are loaded together, the load safety block 208 prevents the actuator 100 and the intermediate connecting body 200 from making a relative rotation and unloading under an elastic force of the load reset spring 207.

Figure 3:
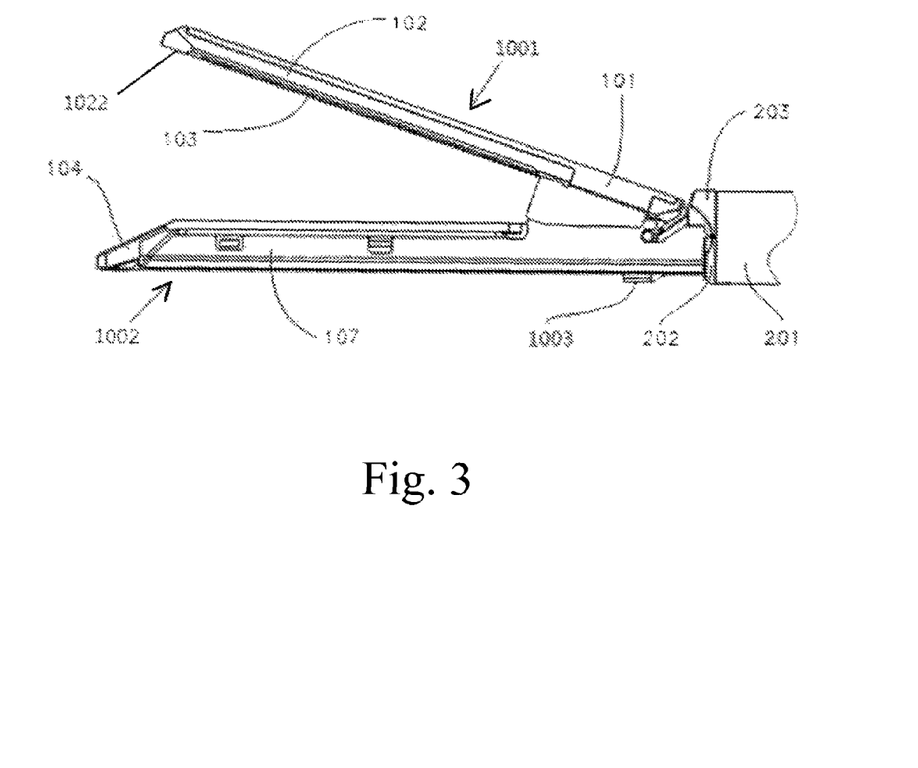
FIG. 3 is a partially enlarged structural schematic diagram for an actuator in the surgical apparatus as shown in FIG. 1.

Refer to FIG. 2-FIG. 3. The actuator 100 mainly consists of a nail anvil assembly 1001, a nail bin assembly 1002 and a drive assembly 1003. The nail bin assembly 1002 usually includes a nail bin 104, multiple suturing nails 105, multiple nail push blocks 106, nail push slides 108 and a nail bin seat 107. An upper surface of the nail bin 104 is a tissue contact surface. The nail bin 104 is installed in the nail bin seat 107. The nail anvil assembly 1001 contains the nail anvil plate 103 and the nail anvil seat 102.

Figure 6:
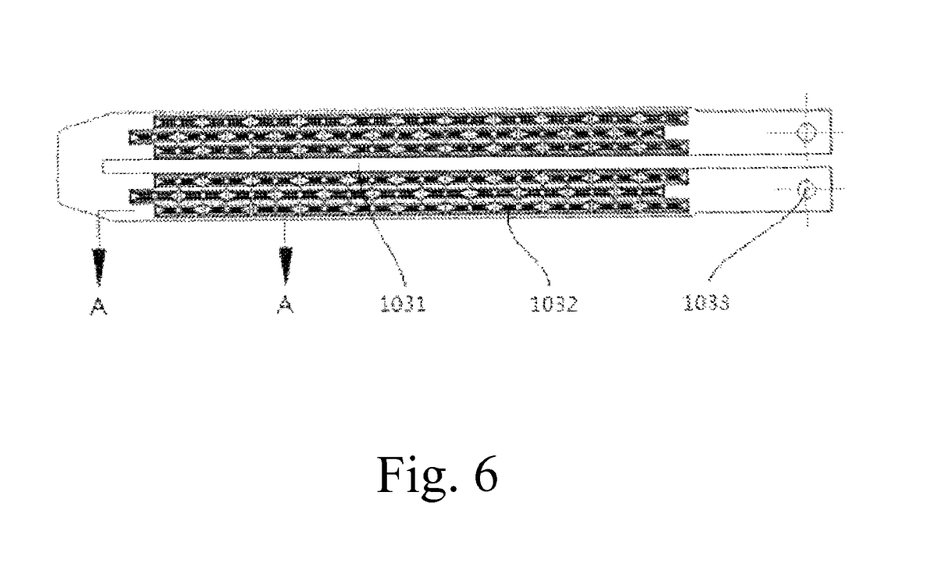
FIG. 6 is a structural schematic diagram for a nail anvil plate in the surgical apparatus as shown in FIG. 1.
Figure 7:
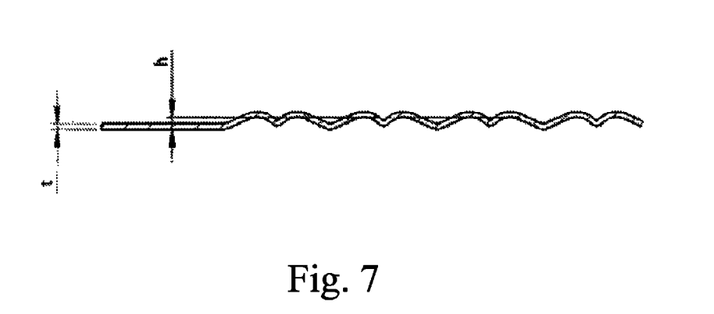
FIG. 7 is a schematic diagram for a partially sectional structure at A-A in FIG. 6 for the nail anvil plate in the surgical apparatus as shown in FIG. 1.
Figure 8:
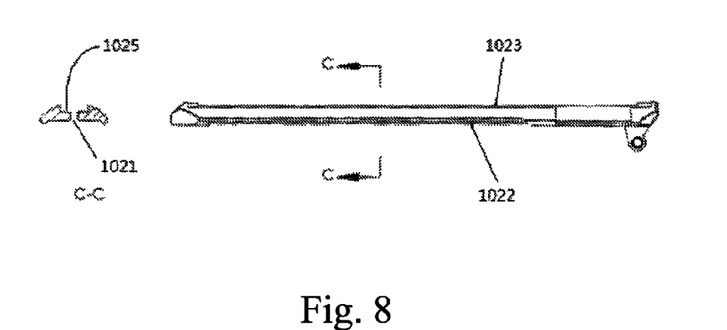
FIG. 8 is a structural schematic diagram for a nail anvil seat in the surgical apparatus as shown in FIG. 1.
Figure 9:
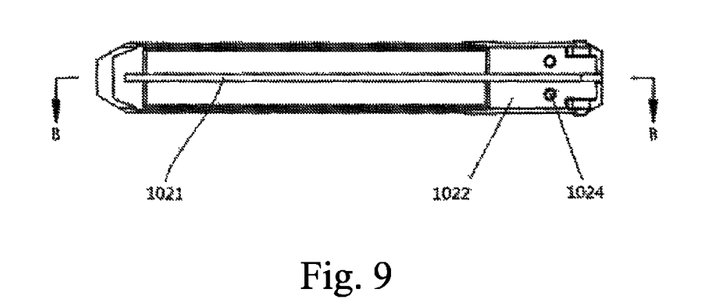
FIG. 9 is a front structural schematic diagram for the nail anvil seat as shown in FIG. 8.
Figure 10:
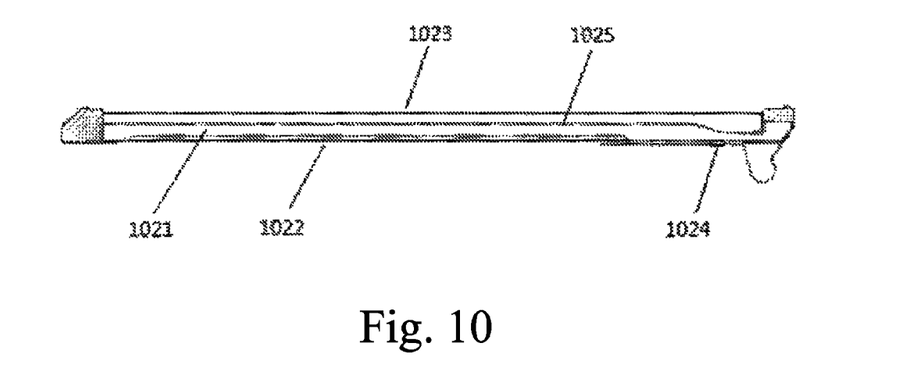
FIG. 10 is a sectional structure schematic diagram at B-B for the nail anvil seat as shown in FIG. 9.

As shown in FIG. 6-FIG. 7, in this embodiment, the nail anvil plate 103 contains a first guide groove 1031 and multiple nail grooves 1032. The drive assembly 1003 can make guided sliding in the first guide groove 1031. The nail anvil plate 103 contains multiple rows of nail grooves 1032 on a surface toward clamping tissues. When the suturing nail 105 is driven to move toward the nail anvil plate 103, the suturing nail 105 enters into the nail groove 1032 and is molded into B shape or similar B shape under the guide of the curved surface inside nail groove 1032.

In this embodiment, the nail anvil plate 103 is cold-punched from stainless steel sheet. A thickness t of the stainless steel sheet is lower than a maximum molding depth h of the nail groove 1032 of the nail anvil plate 103, i.e. t<h. In practical applications, for the suturing nail 105 with a diameter of 0.2 mm-0.25 mm, the maximum molding depth h of the nail groove 1032 is usually in a range of 0.4 mm-0.6 mm to ensure that sufficient guide property is provided during molding of the suturing nail 105; for the suturing nail 105 with a diameter of 0.25 mm-0.35 mm, the maximum molding depth h of nail groove 1032 is usually in a range of 0.45 mm-0.7 mm to ensure that sufficient guide property is provided during molding of the suturing nail 105. When the thickness t of the stainless steel sheet for processing the nail anvil plate 103 is smaller than the maximum molding depth h of the nail groove 1032, preferably, the cold punch process for processing the nail anvil plate 103 can use punch drawing process in place of the impressing process used in molding of the nail groove 1032 on a thick plate.

Refer to FIG. 4, FIG. 8-FIG. 10. The nail anvil seat 102 includes an inner side face 1022, an outer side face 1023 and the second guide groove 1021. The nail anvil plate 103 is arranged on an inner side face 1022 of the nail anvil seat 102. The first guide groove 1031 of the nail anvil plate 103 and the second guide groove 1021 of the nail anvil seat 102 are arranged along a same axis Z.

Figure 4:
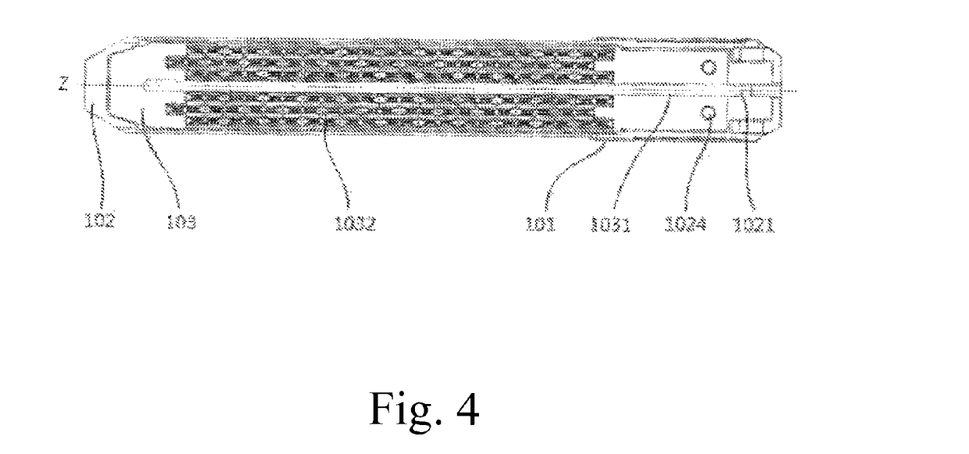
FIG. 4 is a front structural schematic diagram for a nail anvil assembly in the surgical apparatus as shown in FIG. 1.

As shown in FIG. 4, the axis Z is a straight line. At this point, the nail grooves 1032 of the nail anvil plate 103 are arranged in multiple rows of parallel straight lines selectively. The number of the multiple rows of parallel straight lines includes 2 rows-8 rows and preferably 6 rows or 4 rows. In a variation of this embodiment, the difference from the embodiment shown in FIG. 4 is that the axis Z is a curve in this variation. At this point, the nail grooves 1032 of the nail anvil plate 103 are arranged in multiple rows of curves selectively. The multiple rows of curves can be multiple concentric arcs and can also be multiple parallel asymptotes, which can also be curves of other types or a combinational curve of multiple types of curves. The number of the multiple rows of curves includes 2 rows-8 rows and preferably 6 rows or 4 rows. The selective arrangement into multiple rows means that the positions of the nail grooves 1032 are arranged in a staggered manner between the adjacent two rows of the nail grooves 1032.

Figure 5:
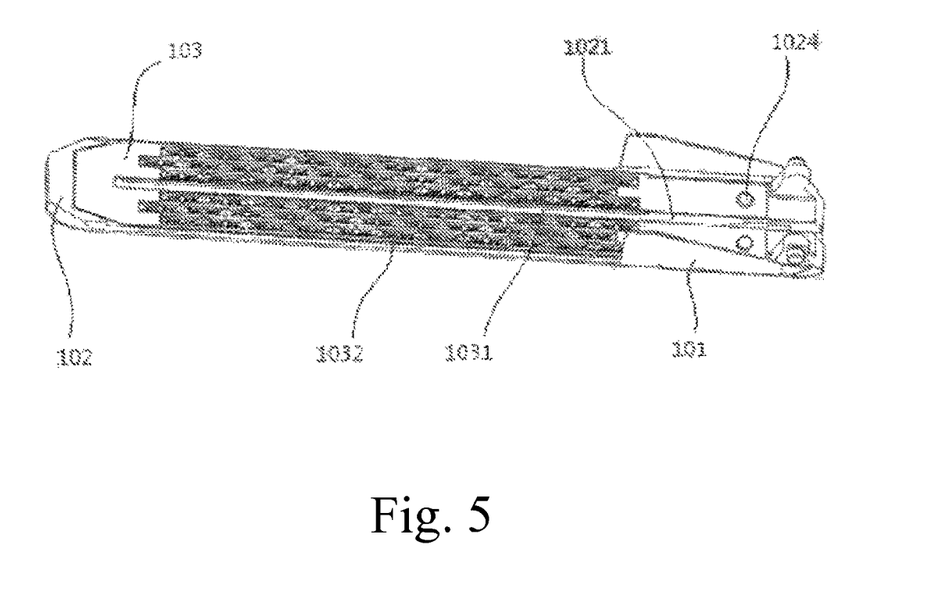
FIG. 5 is a schematic diagram for the three-dimensional structure of the nail anvil assembly in the surgical apparatus as shown in FIG. 1.

To ensure that the nail anvil plate 103 and the nail anvil seat 102 are accurately positioned, as shown in FIG. 4-FIG. 6, a positioning hole 1033 is provided on the nail anvil plate 103 and the positioning pin 1024 is provided on the nail anvil seat 102. The positioning hole 1033 on the nail anvil plate 103 and the positioning pin 1024 on the nail anvil seat 102 are matched for positioning.

The nail anvil seat 102 is processed through a thermal forging process. In the variation of this embodiment, the nail anvil seat 102 can also be processed through a powder metallurgical molding process or a mechanical cutting process.

The nail anvil assembly 1001 also includes a back cover plate 101, which is arranged on an outer side face of the nail anvil seat 102.

In an optimum example of this embodiment, the assemblies of the nail anvil assembly can be connected into a whole through welding, mechanical riveting and a combination of both. In which, welding includes laser welding, resistance welding, fusion welding, etc.

In another optimum example of this embodiment, the nail anvil plate 103 uses 304 stainless steel and nail anvil seat 102 uses 420 stainless steel. The 420 stainless steel can achieve a tensile strength not lower than 1300 MPa after an appropriate heat treatment process. Usually, the tensile strength of 304 stainless steel is not higher than that of 1050 MPa after H1/2 heat treatment.

Figure 1:
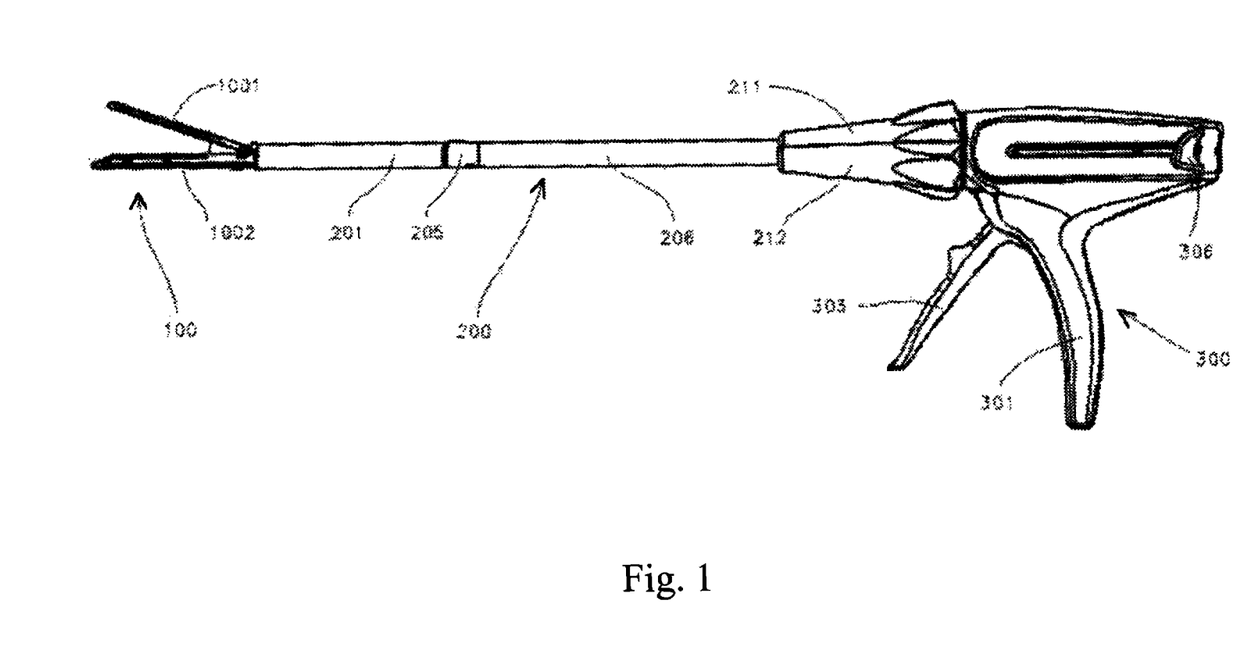
FIG. 1 is a structural schematic diagram of a surgical apparatus improved according to a first embodiment of this invention.
Figure 11:
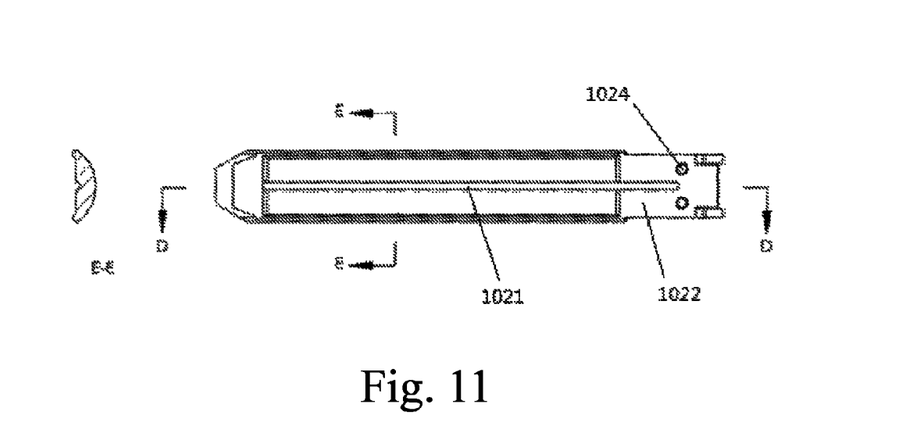
FIG. 11 is a structural schematic diagram for a nail anvil seat in a surgical apparatus improved according to a second embodiment of this invention.
Figure 12:
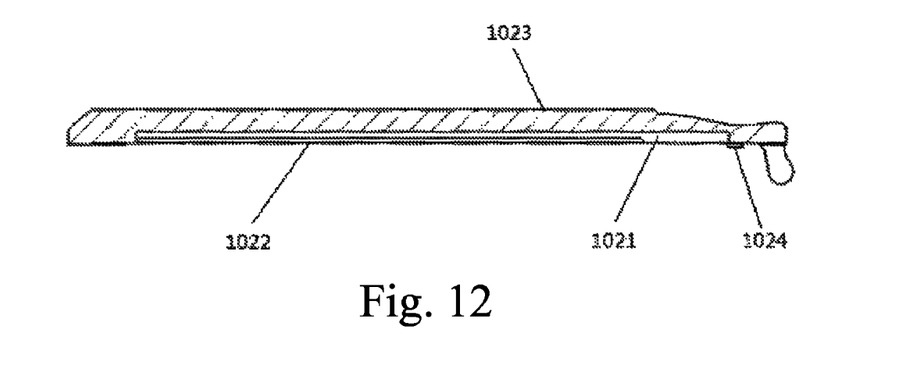
FIG. 12 is a sectional structure schematic diagram at D-D for the nail anvil seat as shown in FIG. 11.

FIG. 11 and FIG. 12 show the schematic diagram of the surgical apparatus improved according to the second embodiment of this invention. The technical people in this field can comprehend the second embodiment as shown in FIG. 12 as a variation of the first embodiment as shown in FIG. 1. Specifically, the difference between this embodiment and the first embodiment as shown in FIG. 1 is that in this embodiment, the back cover plate is omitted. More specifically, as shown in FIG. 11-FIG. 12, the nail anvil assembly 1001 contains the nail anvil plate 103 and the nail anvil seat 102 and does not include the back cover plate. The nail anvil seat 102 includes the inner side face 1022, the outer side face 1023 and the second guide groove 1021. The nail anvil plate 103 is arranged on the inner side face 1022 of the nail anvil seat 102. The first guide groove 1031 of the nail anvil plate 103 and the second guide groove 1021 of the nail anvil seat 102 are arranged along the same axis Z.

The above describes the embodiments of this invention. What need to understand is that this invention is not limited to the above specific embodiments. The technical people in this field can make different variations or modification within the scope of claims and this does not influence the essential contents of this invention.

What is claimed is:

1. A surgical apparatus actuator, comprising a nail bin assembly (1002), a nail anvil assembly (1001) connecting with the nail bin assembly (1002), and a drive assembly (1003) controlling the nail bin assembly (1002) and the nail anvil assembly (1001) to convert between opening and closing conditions, wherein:

the nail anvil assembly (1001) comprises a nail anvil plate (103) and a nail anvil seat (102), wherein the nail anvil plate (103) is provided on an inner side (1022) of the nail anvil seat (102), the nail anvil plate (103) is cold-punched from stainless steel sheet, a thickness of the stainless steel sheet is lower than a maximum molding depth of a nail groove (1032) of the nail anvil plate (103), the nail anvil plate (103) has a first guide groove (1031) provided thereon, the nail anvil seat (102) has a second guide groove (1032) thereon, the first guide groove (1031) and the second guide groove (1032) is arranged coaxially and the drive assembly (1003) slides under a guide of the first guide groove (1031) and the second guide groove (1032);

the thickness of the stainless steel sheet is 0.1-0.4 mm.

2. The surgical apparatus actuator, as recited in claim 1, wherein the thickness of the stainless steel sheet is 0.2-0.3 mm.

3. The surgical apparatus actuator, as recited in claim 1, wherein a material used by the nail anvil seat (102) has a tensile strength higher than that of the stainless steel sheet.

4. A surgical apparatus actuator, comprising a nail bin assembly (1002), a nail anvil assembly (1001) connecting with the nail bin assembly (1002), and a drive assembly (1003) controlling the nail bin assembly (1002) and the nail anvil assembly (1001) to convert between opening and closing conditions, wherein:

the nail anvil assembly (1001) comprises a nail anvil plate (103) and a nail anvil seat (102), wherein the nail anvil plate (103) is provided on an inner side (1022) of the nail anvil seat (102), the nail anvil plate (103) is cold-punched from stainless steel sheet, a thickness of the stainless steel sheet is lower than a maximum molding depth of a nail groove (1032) of the nail anvil plate (103), the nail anvil plate (103) has a first guide groove (1031) provided thereon, the nail anvil seat (102) has a second guide groove (1032) thereon, the first guide groove (1031) and the second guide groove (1032) is arranged coaxially and the drive assembly (1003) slides under a guide of the first guide groove (1031) and the second guide groove (1032);

the nail anvil seat (102) is processed by a method selected from a group consisting of thermal forging, powder metallurgical molding, casting and mechanical cutting.

5. The surgical apparatus actuator, as recited in claim 4, further comprising a back cover plate (101), in which, the back cover plate (101) is provided on an outer side (1023) of the nail anvil seat (102), the outer side (1023) of the nail anvil seat (102) comprises a guide rail surface, an empty cavity exists between the back cover plate (101) and the guide rail surface of nail anvil seat (102) and the drive assembly (1003) moves along a guide rail surface in the empty cavity.

6. The surgical apparatus actuator, as recited in claim 5, wherein all components of the nail anvil assembly (1001) are connected to form an integral structure through welding and/or mechanical riveting.

7. The surgical apparatus actuator, as recited in claim 5, wherein the nail grooves (1032) on the nail anvil plate (103) are arranged in multiple rows of parallel straight lines or parallel curves selectively.

8. The surgical apparatus actuator, as recited in claim 7, wherein the nail grooves (1032) on the nail anvil plate (103) are arranged into 4 rows or 6 rows.

9. The surgical apparatus actuator, as recited in claim 4, wherein all components of the nail anvil assembly (1001) are connected to form an integral structure through welding and/or mechanical riveting.

10. The surgical apparatus actuator, as recited in claim 4, wherein the nail grooves (1032) on the nail anvil plate (103) are arranged in multiple rows of parallel straight lines or parallel curves selectively.

11. The surgical apparatus actuator, as recited in claim 10, wherein the nail grooves (1032) on the nail anvil plate (103) are arranged into 4 rows or 6 rows.

* * * * *